United States Patent [19]
Hawkinson

[11] Patent Number: 5,951,287
[45] Date of Patent: Sep. 14, 1999

[54] DENTAL IMPLANT FAILED FASTENER RECOVERY SYSTEMS, DEVICES AND METHODS

[76] Inventor: Roy T. Hawkinson, 5875 Wing Croft Ct., Bloomfield Hills, Mich. 48301

[21] Appl. No.: 09/060,772

[22] Filed: Apr. 15, 1998

Related U.S. Application Data

[60] Provisional application No. 60/044,078, Apr. 17, 1997.

[51] Int. Cl.⁶ .................................................. A61C 8/00
[52] U.S. Cl. ........................... 433/173; 433/141; 433/172
[58] Field of Search .................................. 433/172, 173, 433/174, 175, 141; 81/53.2

[56] References Cited

U.S. PATENT DOCUMENTS

| | | | |
|---|---|---|---|
| D. 353,674 | 12/1994 | Jorneus | D24/156 |
| 2,694,328 | 11/1954 | La Freniere | 81/53.2 |
| 4,027,392 | 6/1977 | Sawyer et al. | 433/174 |
| 4,324,550 | 4/1982 | Reuther et al. | 433/174 |
| 4,330,891 | 5/1982 | Branemark et al. | 623/16 |
| 4,763,788 | 8/1988 | Jorneus et al. | 206/438 |
| 4,824,372 | 4/1989 | Jorneus et al. | 433/174 |
| 4,907,969 | 3/1990 | Ward | 433/173 |
| 5,015,186 | 5/1991 | Detsch | 433/173 |
| 5,030,095 | 7/1991 | Niznick | 433/173 |
| 5,049,073 | 9/1991 | Lauks | 433/173 |
| 5,064,375 | 11/1991 | Jorneus | 433/229 |
| 5,064,425 | 11/1991 | Branemark et al. | 606/72 |
| 5,069,622 | 12/1991 | Rangert et al. | 433/173 |
| 5,080,589 | 1/1992 | Oden et al. | 433/202.1 |
| 5,098,293 | 3/1992 | Loof et al. | 433/165 |
| 5,100,323 | 3/1992 | Friedman et al. | 433/173 |
| 5,106,300 | 4/1992 | Voitik | 433/173 |
| 5,108,288 | 4/1992 | Perry | 433/173 |
| 5,110,292 | 5/1992 | Balfour et al. | 433/173 |
| 5,125,840 | 6/1992 | Durr et al. | 433/173 |
| 5,125,841 | 6/1992 | Carlsson et al. | 433/213 |
| 5,145,371 | 9/1992 | Jorneus | 433/173 |
| 5,154,612 | 10/1992 | Carlsson et al. | 433/173 |
| 5,169,308 | 12/1992 | Kvist | 433/173 |
| 5,259,759 | 11/1993 | Jorneus et al. | 433/173 |
| 5,269,685 | 12/1993 | Jorneus et al. | 433/174 |
| 5,302,127 | 4/1994 | Crisio, Jr. | 433/173 |

(List continued on next page.)

OTHER PUBLICATIONS

Worthington et al, "Osseointegration In Dentistry An Introduction", pp. 37–46; 86–88; 93–97; 105; 114; 121–123; 126–133.

Taylor et al, "Laboratory Techniques for the Branemark System", pp. 10–15; 53–55;62–63; 68–70.

*Primary Examiner*—John J. Wilson
*Attorney, Agent, or Firm*—Reising, Ethington, Barnes, Kisselle, Learman & McCulloch

[57] ABSTRACT

Dental implant system, method and apparatus of the type wherein an implant fixture is configured at least at a distal end thereof for implanted anchoring in a jawbone of a patient and has an internally threaded bore axially disposed therein and opening centrally through a gingival end of the fixture. A threaded fastening member having a distal end portion, an axially opposite gingival end portion and an externally threaded shank portion located axially between the end portions is removably threadably engaged in the internal threads of the fixture bore. A retrieval passageway extends axially in the fastening member and opens at axially opposite ends in the respective end portions of the fastening member. The passageway has a uniform cross sectional configuration throughout its axial extent in at least the fastener distal end portion whereby an in situ fractured distal end portion segment of the fastening member, when remaining in the fixture bore after removal of the associated gingival end portion fractured fastener segment from the fixture bore, can be retrieved by inserting the working end of a specially related retrieval tool into the access opening formed by the retrieval passageway intersecting the fracture surface of the distal end portion segment to thereby unscrew and thus retrieve the distal end portion segment from the fixture bore. Various improved embodiments of such retrieval tool and implant fastening screw are also disclosed.

31 Claims, 3 Drawing Sheets

U.S. PATENT DOCUMENTS

| | | | |
|---|---|---|---|
| 5,312,253 | 5/1994 | Chalifoux | 433/173 |
| 5,336,090 | 8/1994 | Wilson, Jr. et al. | 433/172 |
| 5,350,300 | 9/1994 | Gallais | 433/173 |
| 5,362,234 | 11/1994 | Salazar et al. | 433/169 |
| 5,527,182 | 6/1996 | Willoughby | 433/172 |
| 5,538,426 | 7/1996 | Harding et al. | 433/172 |
| 5,564,924 | 10/1996 | Kwan | 433/173 |
| 5,591,029 | 1/1997 | Zuest | 433/173 |
| 5,651,675 | 7/1997 | Singer | 433/172 |
| 5,674,072 | 10/1997 | Moser et al. | 433/173 |
| 5,690,489 | 11/1997 | Carchidi | 433/174 |
| 5,704,788 | 1/1998 | Milne | 433/173 |
| 5,716,215 | 2/1998 | Blacklock | 433/173 |
| B1 5,069,622 | 9/1994 | Rangert et al. | 433/173 |

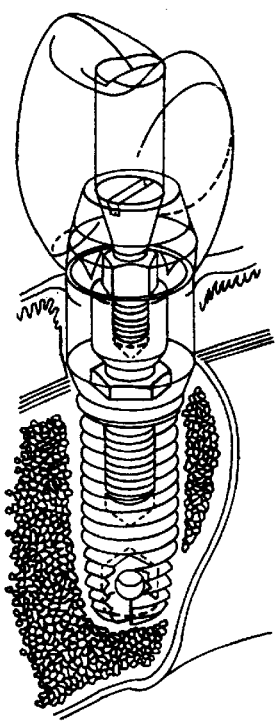

(PRIOR ART)
FIG. 1

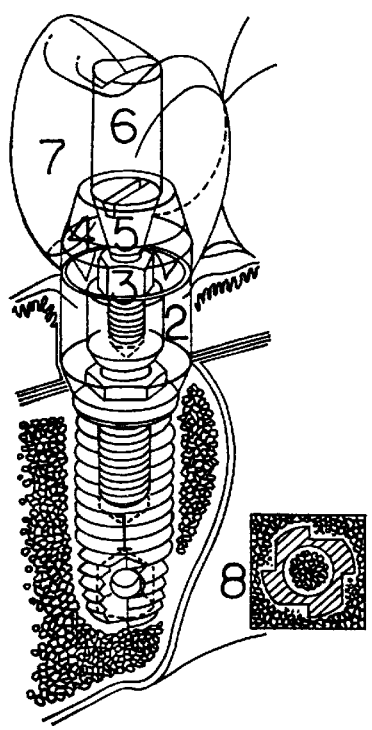

Connection of restoration to implanted fixture:
(1) titanium fixture implanted in the mandible;
(2) titanium abutment passing through the mucosa; (3) titanium abutment screw passing through the abutment; (4) gold cylinder;
(5) gold screw fastening the cylinder to the abutment screw; (6) access hole for gold screw;
(7) artificial tooth of denture; (8) cross section of implant in bone.

(PRIOR ART)
FIG. 2

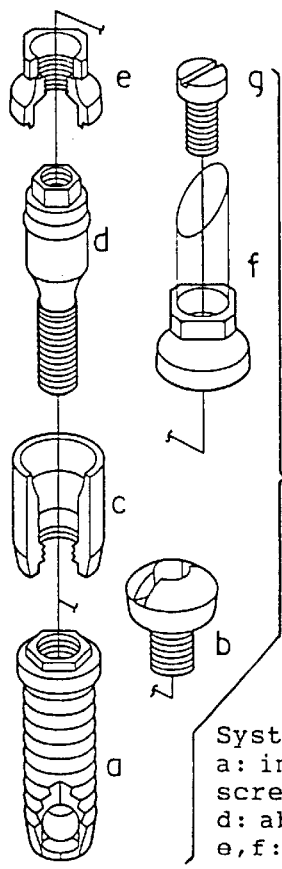

(PRIOR ART)
FIG. 3

Brånemark
System components.
a: implant; b: cover screw; c: abutment;
d: abutment screw;
e, f: cylinders;
g: gold screw.

DENTAL IMPLANT FAILED FASTENER RECOVERY SYSTEMS, DEVICES AND METHODS

This application claims the benefit under 35 USC 119 (e)(1) of U.S. provisional patent application Ser. No. 60/044,078 filed Apr. 17, 1997.

FIELD OF THE INVENTION

The present invention relates generally to implant restorative dentistry and more particularly to prosthodontic restoration systems having components that can be assembled and disassembled utilizing various forms of retention screw fasteners.

BACKGROUND OF THE INVENTION

Various implant-related devices and systems have been created in recent years in an effort to anchor dental prostheses more directly and flexibly in the mandible or maxilla than was possible using conventional dentures or bridges. A scientific breakthrough in the area of dental implants was achieved by Swedish Professor Per-Ingvar Branemark and coworkers. Combining a two-stage surgical technique with the use of titanium fixtures, these scientists achieved predictable results in surgical placement of permanent dental implants. Their continued studies in the early 1960's provided the basis of modern implantology. Such dental implant systems typically employ an anchor fixture or "implant" which has been inserted into the bone and from which extends prosthesis-supporting structure typically coupled to the implant using a fixation screw or other desired fastener. FIGS. 1, 2 and 3 illustrate a typical Branemark implant system that is described in the legends accompanying FIGS. 2 and 3, and that is currently commercially available.

In the three decades that have elapsed since the pioneer Branemark work, extensive research and development effort has gone into efforts to improve and perfect such endosseous implants. Today such implants are basically of three different types: blades, screws and cylinders. Screws and cylinders both require that a hole be drilled into jawbone. In the case of screws, the hole is then either tapped to accept a threaded screw implant or a self-tapping screw implant is threaded thereinto. This latter type is illustrated in FIGS. 1, 2 and 3. A cylinder-type implant having a threaded central bore is installed by first drilling a hole into the bone. The cylinder implant is then introduced into the hole and forcibly tapped into place with a small mallet. With both screw and cylinder type implants, a cover or sealing cap screw is threaded into the open bore of the cylinder to protect and seal the top of the cylinder following first stage surgery implantation. At a later stage of the implantation installation, an abutment, which is typically a hollow cylinder with a central bore, is placed on top of the cylinder through the gum tissue located above the bone to provide a platform for a replacement tooth or artificial dental appliance. An abutment screw extending through the abutment into the implant threads, and a gold prosthetic retaining screw extending through the prosthetic device and into the upper end of the abutment screw, are respectively used to secure the abutment and prosthetic device in place in the implant component assembly.

Thus, as stated in "*Osseointegration in Dentistry An Introduction*" by Worthington, Lang and LaVelle, published by Quintessence Books, copyright____, at page 37:

"There is an apparent lack of consensus among researchers regarding the basic design of an implant, as evidenced by the multiplicity of implant designs. Some state that it is critical to load the bone in compression while minimizing the shear forces; the screw-type implants reflect this theory. On the other hand, proponents of cylindrical designs stress the importance of the implant deriving its support through shear forces applied to the implant-to-bone interface; the cylindrical press-fit implants reflect this theory."

For further background on the history and relatively current state of the art, see the extensive discussion in the Willoughby U.S. Pat. No. 5,527,182 issued Jun. 18, 1996 and incorporated herein by reference.

However, regardless of the type of dental implant design currently being made commercially available, almost all such systems employ some type, and usually a plurality of different types, of fixation screws to retain the implant components in assembly in order to permit removal, repair, restoration, etc., of the implant components as well as to retain the cover screw or healing cap during the first stage surgery, followed by the second stage surgery and abutment connection. Although cementable retained prostheses are an alternative to screw retained prostheses, nevertheless screw-retained abutments are most popular due to their many advantages and represent the most popular type system offered by almost every prosthetic dental implant company. Nevertheless screw-retained systems present long standing and well recognized problems of screw breakage and fracture. To quote the Willoughby '182 patent at column 27, lines 6–10:

"For those clinicians who are placing implant assembly systems, the second worst feeling next to a loosening implant is that of a loosening abutment—one that has loosened because the fixation screw holding it in place has broken or come loose."

Continuing at lines 25–38:

"More often than not, when screws break, they break off at the thread which leaves them submerged in the implant. This makes them very difficult to remove without damaging the implant. The inventor has seen many interesting techniques for retrieving broken screws, but all it takes is to damage a single thread of just one implant and potentially an entire case can be put in jeopardy.

"It can be argued that the only reason these screws break is because of poor treatment, planning and excessive occlusal overloading of the implant assembly. However, the inventor has seen numerous cases of screw breakage—everything from the screw-retained single tooth, to a screw retained dolder bar supported by six implants."

In addition, at column 58, lines 4–14, the Willoughby '182 patent quotes an article by Monteith regarding the results of the University of Toronto's 1990 longitudinal implant study:

"One noticeable feature among the problems and complications encountered during the Toronto study was the large number of gold screws that were reported to have fractured. Of 274 implants that were placed to support 49 protheses, 53 fractures of the gold alloy screws were noted, 14 framework fractures and 9 abutment screw fractures. Similar observation emerged from a replication study conducted at the University of the Witwatersrand in which Shakelton et al. reached the conclusion that more than 50% of prosthetic problems are related to stress factors acting on the prostheses . . . To have screws fracturing as a normal event would not be conducive to sustained levels of patient confidence."

As further stated at column 67, lines 59–67 and continuing at lines 1 and 2, column 7, of the '182 patent:

"At an implant symposium (September 1993) in New York USA when the topic of discussion was confined to implant failures, Dr. Carl Misch was quoted as saying, "Screws rattle loose." (Indirect Verbal Communication.) This is true, but not only do they come loose, they also fracture. This fracturing, which has been reported repeatedly in the literature, is due to biomechanical overload which frequently causes the weakest link in the system to break. In the inventor's opinion, to have screws fracturing as a normal event is no way to maintain patient confidence or deal with the problem of biomechanical overload."

Further recognition of the screw breakage problem is set forth in the aforementioned Worthington et al textbook, *Osseointegration in Dentistry*, at page 39, FIG. 4-2, illustrating an implant complex with a fractured prosthetic retaining screw, caused by exceeding the mechanical limits of the screw. Further, at page 121 of this work, dealing with the status of the implant prosthesis at the recall appointment, the text states:

"The conditions most frequently seen during periodical recall appointments which require attention are gingivitis, soft tissue hyperplasia, small fistulae, exposed implant threads, fracture of the abutment screw, fracture of the anchorage mechanism between the prosthesis and the abutment, loss of optimal occlusal contacts, and fracture of the prosthodontic framework."

The breakage problem as it relates to installing and removing the healing cap or cover screw that is placed in the interval between surgery and abutment selection/prosthesis fabrication is also recognized in the Wilson et al U.S. Pat. No. 5,336,090 which points out at column 2, lines 66–68 and continuing in column 3, line 1:

"Furthermore, because of the excessive torque sometimes used to tighten the healing cap on the fixture, breakage of the fixture and/or the healing cap can occur."

To the same effect is the Salazar et al U.S. Pat. No. 5,362,234, in citing the observation of Desjardeins in a publication entitled "Dental Implant and Prosthodontics", J. B. Lippincott Company, 1991:

"The most common prosthesis problem that the author has thus far noted is the loosening or breakage of the gold locking screw with the resultant loosening of the prosthesis."

Additional patents presenting a sampling of those concerned with the problems of loosening or breakage of the fastening elements in the implant assembly components are:

| Voiteik | 5,106,300 |
| Perry | 5,108,288 |
| Kyist | 5,169,308 |
| Milne | 5,704,788 |

Even in the ordinary every day experience of the automotive mechanic, machinist or tool and die set-up man, the breakage of a screw or a bolt, leaving the threaded leading end fragment of the bolt or screw shank threadably embedded and recessed down into the hole of the female threads in the receiving member, presents a very vexing problem. One can only imagine how this is compounded by orders of magnitude due to the difficulties of dealing with the miniaturized components of an implant assembly located in a difficult location of limited accessibility in the mouth of a patient. Typically, when a screw is fractured off inside the implant fixture, the clinician tries to cut a slot or hole in the bottom of the broken section of the screw so that it can be unscrewed from the fixture. However, to try and tease the broken piece out with a tip of a small instrument, such an explorer, scaler, etc., which is often the general method used today to retrieve these broken pieces, is to say the least a very difficult procedure for both the clinician and the patient. Moreover, such "fishing" efforts can result in the tip of such retrieval tools scarring the internal threads of the implant fixture as the tool tip is being inserted thereinto when trying to cut a hole in the broken section and/or while trying to tease out the broken piece. Damage to the internal threads of the implant fixture can, of course, jam and block the unscrewing of the broken off shank of the fastener, further compounding the problem, as well as ruining the fixture in situ.

OBJECTS OF THE INVENTION

Accordingly, among the objectives of the present invention are to provide improvements in implant system fasteners and related improved methods and devices that render it possible to easily remove the various types of implant fasteners in the event that the same are fractured off inside the implant fixture or other associated implant component, that is adaptable to various types of implant fasteners currently in widespread use, that can be provided at minimum cost, and that provides a safe and effective procedure and retrieval implements for rapidly and reliably solving a various serious problem, i.e., a screw fastener fracture at any stage in the implant installation or after patient use at recall.

BRIEF DESCRIPTION OF THE DRAWINGS

The foregoing as well as additional objects, features and advantages of the present invention will become apparent from the following detailed description of the best mode presently known to the inventor of making and using the invention, from the appended claims and from the accompanying drawings wherein:

FIGS. 1, 2 and 3 are diagrams (with accompanying legends) reproduced from current publications illustrating a prior art single tooth implant system provided in accordance with the Branemark system currently commercially available and provided by way of environmental background information for the invention.

DETAILED DESCRIPTION OF PREFERRED EMBODIMENTS

Background and Environmental Structure

Figure 4:
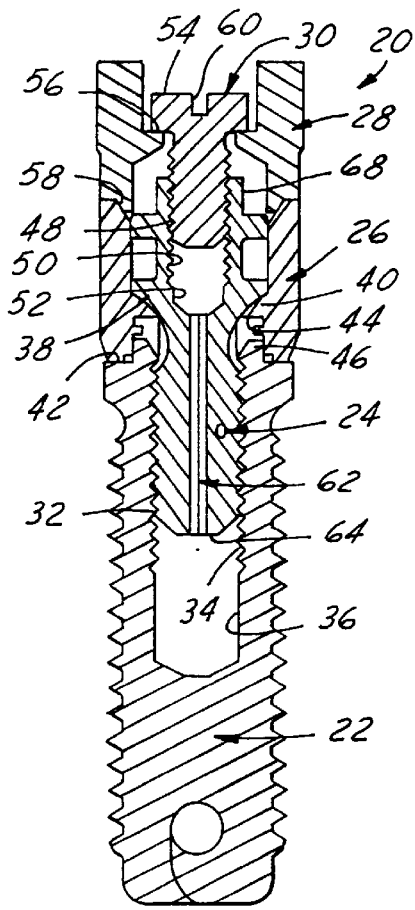
FIG. 4 is a central longitudinal section through an improved implant assembly shown by itself embodying an improved abutment screw provided in accordance with the invention.

Referring in more detail to the accompanying drawings, FIGS. 1, 2 and 3, as previously indicated, illustrate currently commercially available Brånemark system implant components as assembled and implanted in FIGS. 1 and 2, and as described in the legend of FIG. 2 per the reference numerals therein. FIG. 3 is an exploded perspective view of such system components as identified by the legend therein, and include the cover screw (b) for use following first stage surgery and subsequently replaced by the components (c) through (i), as is well understood by those skilled in the art. For further background information, see the aforecited publications "*Ossceointegration in Dentistry An Introduction*". See also the publication "*Laboratory Techniques for the Brånemark System*", by Ross Taylor and Gary Bergman, published by Quintessence Books (copyright_____).

FIG. 4 shows in longitudinal center section an assembly 20 of the implant system components by itself without the prosthetic framework, i.e., artificial tooth 7 of FIG. 2 mounted thereon, and employing an abutment screw made in accordance with a first embodiment of the present invention. Implant assembly 20 thus comprises an implant fixture 22 of the self-threading screw type, an abutment screw 24, an abutment 26, a prosthetic coping 28, and a prosthetic retaining screw 30.

Abutment screw 24 has precision external threads 32 that threadably engage precision internal threads 34 provided in a central blind bore 36 in implant fixture 22. A conically surfaced shoulder flange 38 of abutment screw 24 seats on the mating surface of an internal shoulder 40 of abutment 26 to clamp the lower end face of abutment 26 against an annular seating surface 42 provided on the upper (gingival) end of fixture 22. Abutment 26 has a hexagonal socket 44 in its lower end face that receives a mating hexagonal nut protrusion 46 provided on the upper end of fixture 22 to thereby lock abutment 26 against rotation relative to the fixture. Retaining screw 30 has precision external threads 48 that threadably engage mating internal threads 50 provided in a central blind bore 52 formed in the head of abutment screw 24 and opening at the upper (gingival) end thereof to receive screw 30. A head 54 of screw 30 bears on an internal flange shoulder 56 of coping 28 to clamp the lower square/chamfer end of the coping onto a mating seating surface 58 provided on the upper end of abutment 26. Screw head 54 is provided with a screw driver slot 60 for rotating screw 30.

It will be seen that an interface exists between each of the six components of implant assembly 20 across which functional loads are transferred from the prosthetic framework (item 7 in FIG. 2) mounted on coping 28 and ultimately transmitted to the supporting bone (FIGS. 1 and 2). These six force transfer sites are called prosthodontic interfaces and include the prosthetic coping/abutment interface at surface 58, the abutment screw/prosthetic retaining screw interface between threads 48 and 50, the abutment screw/abutment interface between shoulders 38 and 40 of abutment screw 24 and abutment 40, the abutment/implant interface at surface 42 of fixture 22, and the abutment screw/implant fixture interface between threads 32 and 34 of the abutment screw 24 and fixture 22. Three additional interfaces not shown in FIG. 4 include the interface between the masticatory surface and the artificial tooth 7 of the denture (FIGS. 1 and 2) and occlusal engagement therewith, the interface between the aesthetic veneer of artificial tooth 7 and its substructure, and the interface between the tooth substructure and the prosthetic coping. These nine force transfer sites each plays a significant role in the dynamic state of the biomechanics related to the implant.

As reported in "*Osseointegration in Dentistry*", supra, studies have been conducted that deal with several of these biomechanical areas, including the stress and strength considerations of abutment and prosthetic retaining screws as set forth at page 59:

"Research on implant screws has involved primarily two areas: the ultimate failure strength of the various screws, and the preload torque (clamping force) applied to these screws (FIG. 4-2). This research has been stimulated by two factors: (1) the introduction of an increasing number of similarly designed implant components based on the system originally developed by P. I. Brånemark, and (2) by the recent introduction of torque wrenches that help the clinician uniformly join the implant components to more evenly distribute the forces. Manual tightening of screws can be inconsistent, while mechanical torque-applying devices insure uniform tightening. However, the optimum torque is still controversial, and the theoretical recommendations do not tend to agree with in vitro research reports. The recommendation of a 10-Ncn preload to unit a prosthesis framework or single tooth component to the abutment using the appropriate screw is based on a theory that this 10-Ncn preload is just below the yield strength (the point at which permanent deformation increases rapidly without a corresponding increase in applied load) of the retaining screw and therefore will not cause it to break. However, in vitro research findings have suggested that the optimum preload may be higher. Both the theoretical and in vitro research agree that the optimum preload for a given type of screw should be correlated with the mechanical properties of the specific screw." (footnote omitted)

Suffice it to say herein that, as cited previously hereinabove, the problem of in situ fracture of implant screws, whether they be the primary abutment screw (item 3 of FIG. 2 and item d in FIG. 3), the cover screw (item b of FIG. 3) and/or the gold prosthetic retaining screw (item 5 of FIG. 2 and item g of FIG. 3), remains as a serious and long standing problem well recognized in the art.

If the fracture plane in any one of these screws is located recessed within the mating threads of the associated threaded component, the general method used to retrieve these broken pieces involves a very difficult procedure. Typically this involves trying to cut a slot in the fracture surface of the embedded broken section of the screw to provide an engagement surface so that it can be unscrewed from its associated component. Trying to tease the broken piece out with the tip of a small dental instrument, such as an explorer, scaler, etc., is extremely difficult and delicate procedure even on the lab bench due to the miniature size of these components, and of course even more difficult and hazardous when in the adverse operating environment in which they are usually found, i.e., the mouth of the patient. If such retrieval efforts prove unsuccessful, surgical removal of the entire implant fixture from the implant/bone-interface often becomes necessary. However, the present invention overcomes this serious problem of retrieval of the fractured or broken in situ screw segment in a very expeditious, economical and reliable manner.

First Embodiment Implant Assembly and Method

Figure 5:
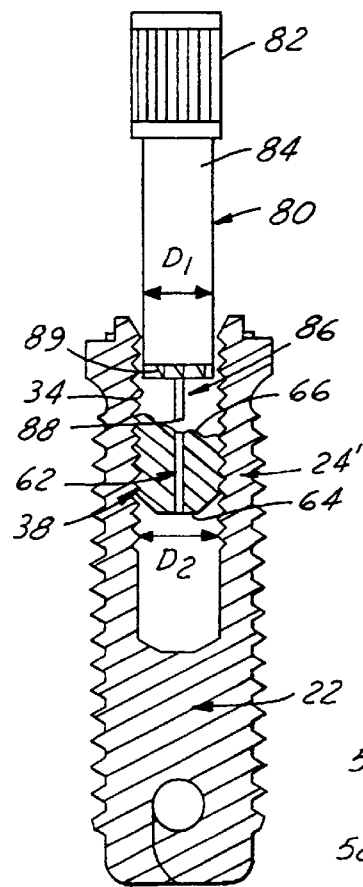
FIG. 5 is a center longitudinal section of the implant fixture of the FIG. 4 assembly but illustrating a fractured lower end segment portion of the abutment screw of FIG. 4, and also the use of an improved abutment screw retrieval tool constructed in accordance with the invention.
Figure 6:
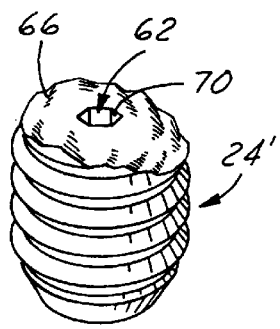
FIG. 6 is a simplified perspective view on an enlarged scale of the broken segment piece of the abutment screw of FIG. 5 shown by itself after removal from the fixture.

Thus, in accordance with the principal feature of the present invention, in the system of FIG. 4, abutment screw 24 is provided with a central, axially extending retrieval passageway 62 that opens at its upper (gingival) end into bore 52 and opens at its lower end at the bottom (distal) end face 64 of screw 24. The cross sectional configuration of retrieval passageway 62 may take several forms, as described hereinafter in conjunction with FIGS. 11–16, but in the embodiment of FIGS. 4–6 is of hexagonal configuration.

Preferably, in accordance with the method of the invention, passageway 62 is formed initially in the rod or bar stock metal from which the various geometrically finished surfaces of abutment screw 24 are subsequently to be precision machined, such as in an automatic Swiss screw machine. Preferably, the stock metal is provided in bar or rod shape and then extruded in a conventional multiple stage extrusion process to first form both the O.D. and the through passageway 62 oversize, with the hexagonal cross sectional contour core-extruded into passageway 62. Then this preform is drawn through a smaller die (ensmalling die) to reduce the O.D. and hence also the cross sectional dimension of passageway 62 to the proper final size. The subsequent screw machine manufacturing process is employed in finishing the external configuration and various external surfaces and external threads of the abutment screw 24.

By employing such conventional metal processing techniques, the strength of abutment screw 24 need not be reduced by the presence of retrieval passageway 62, particularly if work hardening by cold extrusion is employed in a conventional manner, and/or appropriate heat treatment is utilized. Moreover, the location of passageway 62 coincident with the axis of the screw does not impair the torsional strength of the screw because the material removed is along the neutral torsional axis of the structure. Indeed, judicious selection of materials and CAD/CAM machine, or other automated metal processing techniques utilized in a conventional manner by those skilled in the art should even enable enlargement of passageway 62 over the scale of that shown in FIG. 4 in at least some applications without increasing the in situ fracture hazards.

With the foregoing provision of retrieval passageway 62 extending throughout the axial length of the body of abutment screw 24, i.e., its externally threaded portion, it will be seen that regardless of the location of the screw fracture plane recessed among the internal threads 34 of fixture 22, a ready-made retrieval hole will appear in the fracture surface.

More particularly, and referring to FIGS. 5 and 6, implant fixture 22 is illustrated with a broken off distal end segment 24' of screw 24 remaining entrapped in threaded engagement with threads 34 of fixture 22. It will be seen that the site of the fracture upper end face 66 of segment 24' is located well below the upper end of fixture 22. Of course, the upper gingival portion of the fractured screw 24 (not shown) already has been removed expeditiously in the usual manner by retrograde rotation applied to its hexagonal upper end nut-form protrusion 68 (FIG. 4).

FIG. 6 illustrates the fractured distal segment 24' shown by itself and wherein it will be seen that a hexagonal opening 70 is now present in the fracture surface 66 due to the preexistence of retrieval passageway 62 extending through the fracture plane as defined by surface 66. With this ready-made hole 70 in the broken portion of the screw that remains threadably lodged in the implant fixture, easy retrieval of segment 24' is now made possible. Preferably, this is performed using a small screw-retrieval instrument also provided in accordance with the invention. The tools of FIGS. 5 and 11–15 are designed for this purpose and have an appropriately configured shank and free end tip constructed and arranged to be inserted into hole 70 in order to back out the broken screw section. The tool shank is merely inserted into bore 36 of fixture 22 to bring the tool tip into seated torque-transfer engagement in passageway 62 and then rotated in the appropriate direction to unscrew segment 24' from threaded engagement with fixture threads 34. Once segment 24' protrudes from the upper (gingival) end of fixture 22 and is clear of such threaded engagement, the same can be retrieved with suitable instruments or merely carried away clear of the patient's mouth on the tip of the tool.

Preferably, and in accordance with a further feature of the system, apparatus and method of the invention, the form of retrieval tool 80 shown in FIG. 5 is provided for effecting the aforementioned retrieval of the fractured abutment screw segment 24' from fixture 22. Tool 80 is generally in the form of a special precision screwdriver having an enlarged narrow fluted head 82 at its manipulating end joined to a smooth surfaced cylindrical shank 84 extending coaxially from head 82. A suitably configured removal tool blade or bit 86 protrudes coaxially from the distal lower end of shank 84 a suitable predetermined distance and terminates in a free end 88. The outside diameter $D_1$ of shank 84 is dimensioned relative to the minimum inside diameter $D_2$ of fixture threads 34 to provide a close clearance sliding fit of shank 84 coaxially into threads 34. Shank 84 thus guides the removal tool 80 while automatically centering the tool tip 86 so that it will be aligned to properly engage the exposed hole opening 70 of retrieval passageway 62 at fracture face 66.

The close fit of shank 84 also protects the internal threads 34 of implant fixture 22 from damage during insertion of tool 80 to retrieval engagement position, and also while the broken segment 24' is being removed by unscrewing it by rotating tool 80 in the unscrewing direction. In other words, without the provision of centering shank 84, the tool tip 86 could be adversely manipulated and thereby possibly scar the internal threads 34 as the tool tip is being inserted into implant fixture 22 when trying to seat tip 86 into hole 70 in the fracture space 66 of the broken screw segment 24'.

As an optional feature, the lower or distal end face of shank 84 may be provided with an annular row of a plurality of suitable buttress form teeth 89, one or more of which would abut and engage fracture face 66 after tip 86 has been telescoped into passageway 62 via hole 70. Such engagement by one or more teeth 89 at points spaced radially outwardly of hole 70 along face 66 will of course increase the torque transmitting capability of tool 80 relative to segment 24', and thereby facilitate retrieval of segment 24' when threads 38 and/or 34 are damaged and/or partially clogged by debris or sediment deposits. Typically the fracture face 66 will not be completely smooth and hence any upwardly protruding burrs that remain on surface 66 may and often will provide ready-made engagement points for one or more of the teeth 89. Any tendency of such tooth-to-segment engagement to impart sideways skewing forces on tool 80 will be adequately resisted by the clearance fit of shank 84 in threads 34 as well as by the piloting effect of tool tip 86 seating in passageway 62. Thread binding therefore will be inhibited by this tool design in its retrieval operation.

In the embodiment of FIGS. 4–6, the cross sectional configuration of tool tip 86 is hexagonal to match the passageway 62 and is made slightly smaller in its cross sectional dimensions to provide a close clearance fit within passageway 62. Of course, the hexagonal complementary configurations of tool tip 86 and passageway 62 impart suitable torque transmission capability between tool 80 and segment 24' for retrieval purposes, either alone or in combination with the enhanced torque transmission capability provided by teeth 89.

Second Embodiment Implant Assembly

Figure 7:
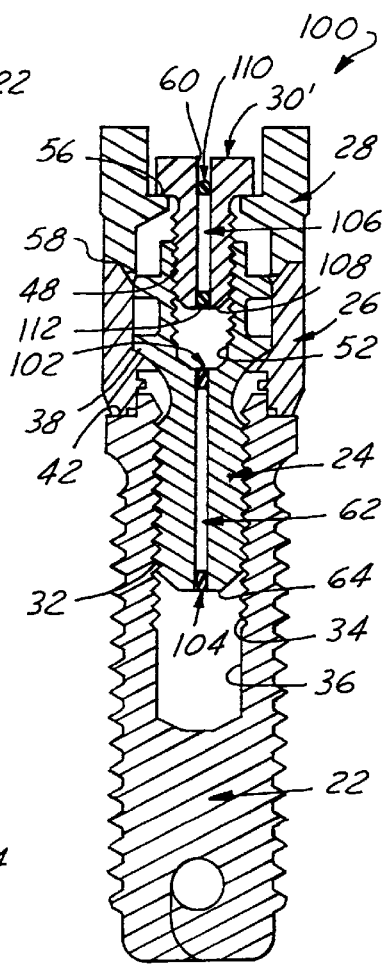
FIG. 7 is a center longitudinal cross sectional view of a second embodiment of an implant system incorporating a modified abutment screw and also a modified prosthetic retaining screw also constructed in accordance with the present invention.

FIG. 7 illustrates a second embodiment implant assembly 100 of the invention which may be identical to assembly 20 except for modifications to abutment screw 24 and retaining screw 30'. In assembly 100, retaining screw 24 may be provided with a suitable passageway seal 102 installed at the upper end of retrieval passageway 62 at its junction with bore 52, and with a second seal 104 inserted into the lower end outlet of passageway 62 at abutment screw distal end face 64. Upper seal 102 may be made of suitable soft sterile or antiseptic plastic material or other dental material of like nature having a resilient press fit into passageway 62, or alternatively could be a soft sterile adhesive. Material choice should allow for seal 102 to be pushed down passageway 62 by insertion of tip 86 of the retrieval tool during broken screw retrieval efforts, should such be necessary. On the other hand, if the fracture plane is located below plug 102, plug 102 will be automatically removed when carried with the upper broken portion of screw 24 as it is removed to access the broken segment 24'. Lower seal plug 104 typically will reside below the lowermost fracture plane encountered and hence not hinder access of the tool tip 86 into the opening 70 exposed by the fracture plane at fracture surface 66, for example. However, if the fracture plane is at or slightly above lower seal 104, the same can be pushed out of passageway 62 when tip 86 is registered and inserted in the same.

Seals 102 and/or 104 serve to prevent sediment and saliva drainage from clogging passageway 62 during use of the implant assembly in the patient's mouth, and also help seal off fluid invasion if and when such drainage and sediment leak past the threads and collect in the bottom of fixture bore 36. In some cases, only the upper seal 102 may be needed if the engagement of threads 32 with threads 34 offers sufficient sealing capabilities to limit accumulation in the bottom of the bore 36 by leakage through the thread engagement.

Implant assembly 100 also incorporates a modified retaining screw 30' which is identical to screw 30 of assembly 20 except that a retrieval passageway 106 is provided centrally and coaxially with the screw body to open at its upper gingival end at screw slot 60 and at its lower end to the distal end face 108 of screw 30'. Retrieval passageway 106 is cross sectionally configured in the same manner as passage 62 and is of like dimensions cross sectionally. If screw 30' is fractured in situ to thereby leave a broken segment below the upper end of abutment screw 24, the broken piece can be removed with tool 80 in the same manner as previously described in conjunction with retrieval of screw fragment 24'. Such in situ fragmentation of coping retaining screw 30' or screw 30 typically is not as disastrous nor present as serious a problem as fracture of abutment screw 24 since screw 30, 30' can be retrieved from an unfractured abutment screw 24 after it is removed from fixture 22. Nevertheless such retrieval itself is an undesirable procedure and may require surgery or other special procedure in order to free abutment 26 from its position after the fixture has stabilized and been in use in the patients mouth. Passageway 106 can also be provided with upper and lower passageway seals 110 and 1 12, respectively, the same being constructed, installed and used in the same manner as seals 102 and 104 described previously.

Third Embodiment Implant Assembly

Figure 8:
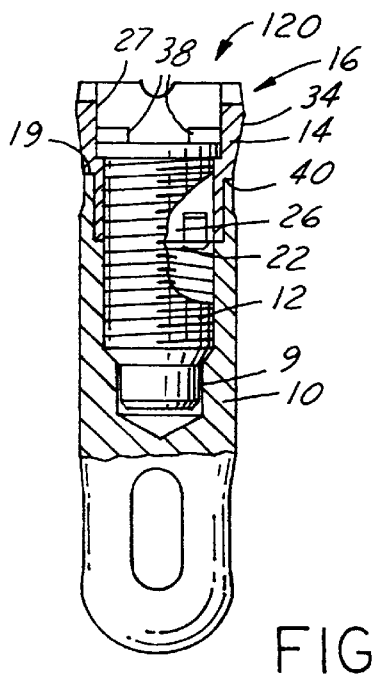
FIG. 8 is a part sectional and part vertical elevational view duplicating FIG. 2 of the Durr et al U.S. Pat. No. 5,125,840 incorporating the reference numerals supplied therein and incorporated herein by reference.
Figure 9:
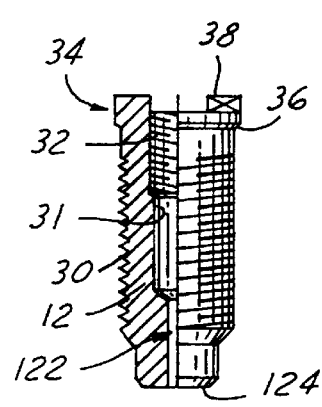
FIG. 9 is a replication of FIG. 3 of the Durr et al U.S. Pat. No. 5,125,840 incorporating the reference numerals employed therein and additionally showing the modification thereof to construct such abutment screw to embody the improvement features of the invention.

FIGS. 8 and 9 illustrate a third embodiment implant assembly 120 of the invention that is first constructed in accordance with the disclosure of FIGS. 2 and 3, respectively, of the aforementioned U.S. Pat. No. 5,125,840, which is incorporated herein by reference. Inasmuch as the same reference numerals are utilized in FIGS. 8 and 9 as those found in FIGS. 2 and 3 of the '840 patent, for brevity the description of the components is not repeated. In accordance with the present invention, abutment screw 34 of assembly 120, shown by itself in FIG. 9, is provided with a retrieval passageway 122 that opens at its upper end coaxially into bore 31 of abutment screw 34, and opens at its lower end in the distal end face 124 of screw 34. Passageway 122 has a cross sectional configuration like that of passageway 62 or like the alternative cross sectional configurations of FIGS. 11–16 described hereinafter. Again, upper and lower end seals such as seals 102, 104, may be provided in passageway 122 for like purposes. It will be noted that the provision of retrieval passageway 122 in the configuration of abutment screw 34 is particularly advantageous inasmuch as the relatively large diameter of bore 31 tends to induce a fracture zone or plane in the vicinity of the blind end of the bore due to the transition in radial cross sectional thickness of the screw and resultant potential stress concentrations in this zone. Since passageway 31 is presumably made by drilling and tapping equipment, retrieval passage 122 can be economically drilled in the same operation, if desired.

Fourth Embodiment Implant Assembly

Figure 10:
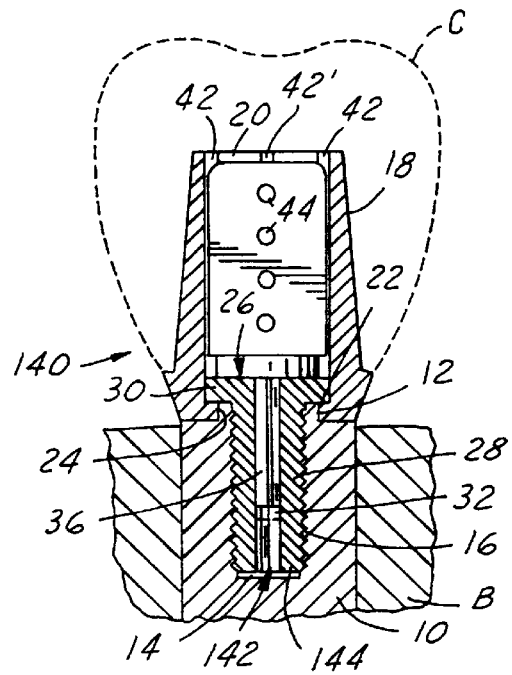
FIG. 10 is a replication of FIG. 2 of the Milne U.S. Pat. No. 5,704,788 incorporating the reference numerals used therein, also incorporated here by reference, and modified to embody the retrieval system of the invention.

FIG. 10 illustrates the application of the features of the invention to the implant assembly structure described in conjunction with FIG. 2 of the aforementioned U.S. Pat. No. 5,704,788, which is also incorporated herein by reference. The same reference numerals as employed in FIG. 2, and the description thereof, in the '788 patent are employed in FIG. 10 and for brevity their description not repeated. Implant assembly 140 also comprises a simple modification of the implant assembly of the '788 patent. As will be evident in FIG. 10, the retrieval passageway 142 of the invention is provided merely as an extension or continuation of the drive socket bore 32 so that the passageway 32/142 extends completely coaxially through the entire length of coping screw 26. Hence passageway 32 opens at the upper end face of the head 30 of screw 26, and continuation passageway 142 opens at its lower end at the lower distal end of face 144 of the shank 18 of screw 26. Since in the '788 patent device the coping screw locking member 34 is normally intended to be provided enclosed in the upper end of passageway 142, there is no need or capability of using an upper end seal 102. However, lower end seal 104 may be provided in the lower end of passageway 142, if such proves necessary to prevent passageway clogging.

The retrieval tool provided by the invention for retrieval of a fractured segment of screw 26 will have a tool tip with a cross sectional configuration complementary to that of retrieval passageway 32/142, i.e., hexagonal or other configuration as described in the '788 patent. Note that, due to the locking engagement of coping screw locking member 34 with the grooves 42 of abutment 18, locking member 34 itself cannot be employed as a retrieval tool because it cannot be rotated relative to screws 26 while captured for anti-rotation engagement with abutment 18. However, if a coping screw locking member 34 were modified to shave off the side edges of blade 40 to clear the I.D. of abutment 18, blade 40 suitably lengthened to better allow manipulation, and likewise shank 36 suitably lengthened, such a readily made modification of member 34 would serve as a retrieval tool in accordance with the present invention for use with assembly 140.

Alternate Embodiments of Retrieval Tools and Associated Abutment Screws

FIGS. 11–16 illustrate various modifications in accordance with the invention that may be made to the retrieval tool and associated abutment screw without departing from the principles and scope of the present invention.

Figures 11, 12:
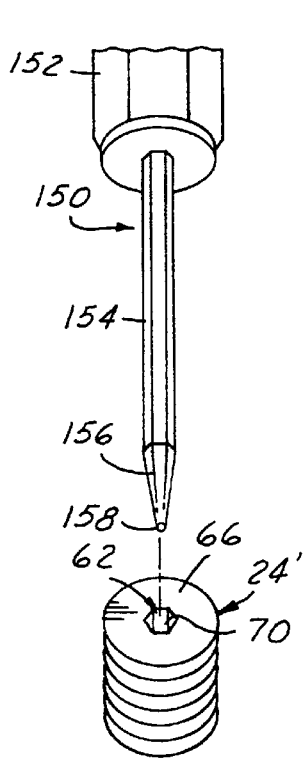
FIGS. 11, 12, 13, 14 and 15 are simplified exploded fragmentary perspective views of various embodiments of abutment screws and associated retrieval tools also further provided in accordance with the invention.

FIG. 11 illustrates the fractured abutment screw segment 24' shown by itself with its hexagonal retrieval passageway 62 exposed at the fracture face 66, thereby leaving the access opening 70, as described previously in conjunction with FIGS. 4–6. The retrieval tool 150 shown in FIG. 11 is constructed similar to a screwdriver with a suitable handle head 152 and an elongated shank 154 of hexagonal cross sectional configuration complementary to that of passageway 62 and having a close sliding fit therein. The free end tip 156 of shank 154 is tapered to a tip point 158 to facilitate locating and insertion of tip 156 into opening 70 followed by telescoping shank 154 therein to provide the torque transmission rotation capability between tool 150 and segment 24' for removal of the same from the associated implant fixture.

FIG. 12 shows the broken off segment 160 of an abutment screw corresponding to segment 24' wherein the abutment screw is provided with a retrieval passageway 162 having a square cross sectional configuration that preferably extends coaxially through the abutment screw for its entire axial length and is open at the opposite axial ends thereof at the axial opposite ends of the abutment screw. The retrieval tool 164 shown in FIG. 12 thus has a modified shank 166 having a square cross sectional configuration complementary to that of passageway 162 and sized for close sliding fit therein, and is provided with the tapered end 156 in the manner of tool 150.

Figures 13, 14:
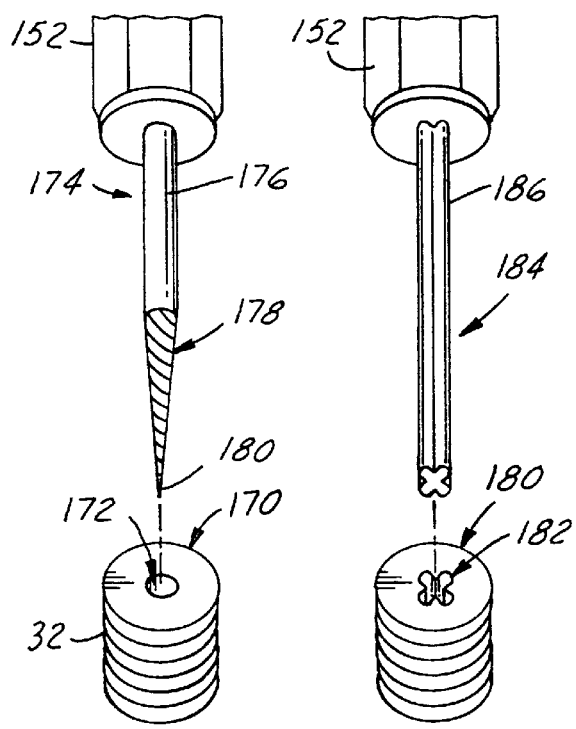

FIG. 13 shows a broken fragment 170 of an abutment screw corresponding to segment 24' wherein the abutment screw is modified so that the retrieval passage 172 preferably extending completely therethrough has a circular cross sectional configuration. The retrieval tool 174 of FIG. 13 has a cylindrical shank 176 protruding from handle 152 that terminates in an auger-threaded tip 178 that tapers to a point 180. Tip 178 is designed in the manner of the well-known "easy-out" retrieval tool well known in the mechanical trades, but is suitably dimensioned in a miniaturized fashion for use in accordance with the invention. Preferably tips 178 as well as shank 176 are made of high strength, hardened stainless steel, and the threads of tip 178 are of the auger-type to be self-threading into the material of abutment screw fragment 170 in passageway 172. The threads are made opposite hand to those of the threads 32 of the abutment screw fragment 170 so that threaded penetration of tip 178 into passageway 172 imparts an unscrewing torque to abutment fragment 170.

FIG. 14 illustrates an abutment screw fragment 180 similar to fragment 24' except that the passageway 182 therethrough has a cruciform or "X" cross sectional configuration. Accordingly, the retrieval tool 184 provided for use in conjunction with abutment screw 180 has a retrieval shank 186 likewise of cruciform or "X" cross sectional configuration complemental to that of passageway 182 and designed for a close sliding fit therein.

Figures 15, 16:
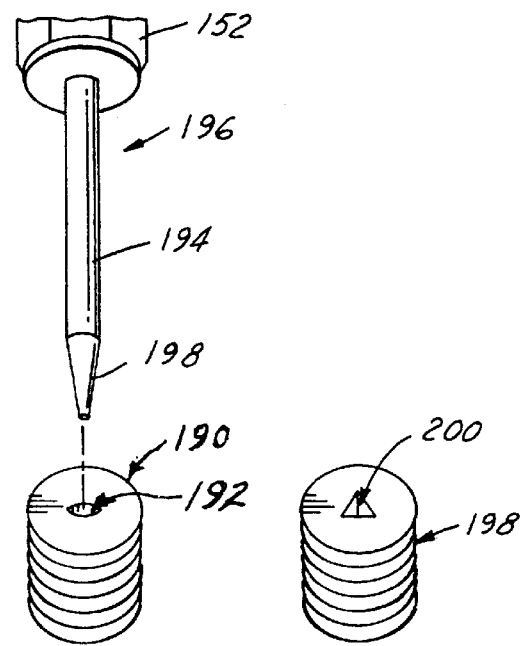
FIG. 16 is a simplified fragmentary perspective view of further embodiment of an abutment screw provided with another form of retrieval passageway in accordance with the invention.

FIG. 15 illustrates an abutment screw fragment 190 corresponding to segment 24' wherein the abutment screw is provided with a retrieval passageway 192 having an oval cross sectional configuration. Likewise, the shank 194 of the associated retrieval tool 196 has an oval cross sectional configuration uniform throughout its axial length complemental to that of passageway 192 and designed for a close sliding fit therein. A pointed and oval configured tip 198 is provided on the leading end of shank 194 to facilitate insertion thereof into the mouth of passageway 192 at the fracture interface of the abutment segment 190.

FIG. 16 illustrates an abutment screw fragment 198 corresponding to segment 24' but having a retrieval passageway 200 of triangular cross sectional configuration. The retrieval tool (not shown) for this modification likewise has a shank of triangular configuration complemental to that of passageway 200 and designed for a sliding fit therein, and again it is provided with a tapered entrance tip of triangular cross sectional configuration.

From the foregoing description and drawing figures as referenced herein it will be apparent to those skilled in the art that the implant system of the invention, and associated retrieval methods and methods of manufacturing and providing the same, amply fulfill the aforestated objects and provide many features and advantages over the prior art.

Each of the implant assemblies incorporates an abutment screw that can be easily removed in the event that the screw is fractured off inside the implant fixture. Likewise, similar features can be provided with respect to the prosthetic retaining screw employed in the assembly in the event it too becomes fractured off inside its associated abutment screw. The retrieval passageway provides an always available access hole for co-rotational engagement of the retrieval tool with the fractured segment of the screw regardless of the location of the fracture point in the screw. The retrieval passageway may be made small enough so that the strength of the screw is minimally affected. The central coaxial location of the retrieval passageway in the screw shank along the neutral axis thereof has little or no affect on the torque capability of the screw. In the case of the implant assemblies 120 and 140, provision of the retrieval passageway may be made in the same machining operations in which the respective abutment screws are formed with little or no additional manufacturing costs.

If desired, the abutment and/or retaining screw may be made of a stronger metal such as PGP (platinum-gold-palladium) to thereby offset any weakness that may be imparted by the provision of the retrieval-through passageway provided in accordance with the invention. In this way, the provision of the abutment screw 24, retaining screw 30 and/or the cover screw b (FIG. 3) may be accomplished in accordance with the invention to provide a screw of the exact same strength as the original screw but with the retrieval passageway incorporated therein.

The system of the invention eliminates the prior frustrating attempts of trying to retrieve an in situ fractured screw, i.e., trying to cut a slit or hole in the broken section of the screw so that it can be unscrewed from its associated fixture. It is no longer necessary to try and tease the broken piece out with the tip of a small instrument such as an explorer, scaler, etc., which is often the general method used hitherto to retrieve these broken pieces, obviously a very difficult procedure and one that is not always successful. For a further and more recent study of the failure of dental implants, see "Comparison of Strength and Failure Mode of Seven Implant Systems: An In Vitro Test"; by Mullerstein et al, J. Prosthetic Dent., 1997; 78; 582–91.

The preferred form of retrieval tool 80 (FIG. 5) provides additional advantages in ease and reliability of use while preventing damage to the internal threads of the associated fixture in which the fractured screw fragment is lodged. As will be seen by the above-described application of the features of the invention to the implant constructions of FIGS. 8, 9 and 10, the invention is readily adaptable to a wide variety of implant designs and constructions, making it possible to retain the advantages of each with the major enhancement provided by the incorporation of the retrieval features of the invention. Indeed, certain features of the invention can be used to advantage even where the retrieval passageway does not extend all the way through the shank of the fastener, i.e., similar to passageway 32 of abutment screw 26 of the system of FIG. 10 as originally designed wherein the passageway 32 terminates in a blind end (shown by dotted lines in FIG. 10). If in such a design the fracture plane occurs above the blind end of the passageway 32, the retrieval tool 80 is suitably re-dimensioned for use in such a fixture assembly and then may be used to advantage in accordance with the invention to retrieve the in situ fractured abutment screw fragment.

Likewise, for certain abutment retainer and a cover screw designs presently conmmercially available, it may well be possible to drill or machine the retrieval passageway as a blind bore opening only at the distal end face of the screw. In such case, the bore blind end serves as a seal and is located axially between the screw gingival end and any zone of potential fracture as determined by screw design and FEA analysis. However, a completely through (opening at both axially opposite ends) retrieval passageway is definitely preferred, both from the standpoint of economy and ease of manufacture as well as providing an always-available portion of the retrieval passage regardless of location of the fracture plane in the abutment screw or design of other screw fastener employed in the implant system.

From the foregoing description, it will be evident that the principles and features of the invention may be widely varied in accordance with the disclosed modificafions. Hence these and other changes may be made, as desired, without departing from the spirit of the invention and scope of the appended claims.

I claim:

1. In dental implant apparatus of the type comprising:
   (a) an implant fixture configured at least at a distal end thereof for implanted anchoring in a jawbone of a patient and having an internally threaded bore axially disposed therein and opening centrally through a gingival end of said fixture, and
   (b) a threaded fastening member having a distal end portion, an axially opposite gingival end portion and an externally threaded shank portion located axially between said ends and removably threadably engaged in the internal threads of said fixture bore, said gingival end portion normally protruding out of the bore opening an including head means thereon configured for rotating said fastening member relative to said fixture by engagement with a fastener rotating tool; the improvement in combination therewith of:
   (c) a retrieval passageway extending axially within said fastening member, said passageway opening at least at a first axial end disposed in the gingival end portion of said fastening member, said passageway having a cross sectional configuration throughout its axial extent in at least said distal end portion whereby an in situ fractured distal end portion segment of said fastening member, remaining in said fixture bore after removal of the associated gingival end portion fractured fastener segment from said fixture bore, can be retrieved by inserting a cooperatively shaped working end of a retrieval tool into the access opening formed by said retrieval passageway intersecting the fracture surface of the distal end portion segment to thereby unscrew and thus retrieve the distal end portion segment from said fixture bore, and wherein seal means is disposed in said retrieval passageway and is constructed and arranged to block flow of liquid or debris past said seal means in said retrieval passageway.

2. The apparatus set forth in claim 1 wherein said retrieval passageway is also open at a second axial end thereof disposed in the distal end portion of said fastenin member, and wherein said seal means is disposed in said first end of said retrieval passageway.

3. The apparatus set forth in claim 2 wherein said seal means is also disposed in said second end of said retrieval passageway.

4. The apparatus set forth in claim 1 wherein said retrieval passageway is also open at a second axial end thereof disposed in the distal end portion of said fastening member, and wherein said seal mears is disposed in said second end of said retrieval passageway.

5. The apparatus set forth in claim 1 wherein said retrieval passageway extends through said gingival end portion and head means and wherein said cross sectionial configuration thereof is uniform throughout the entire axial length of said passageway, and wherein said seal means is disposed in the zone between said externally threaded shank portion and an exterior exposed surface of said head means and is localized in said zone such that removal of the fractured associated gingival end portion segment from the fixture bore carries said seal means with it so that the access opening in the fractured surface of the distal end portion segment remaining is not blocked by said seal means when the fracture plane occurs anywhere in said shank portion between said seal means and said distal end portion most remote therefrom.

6. The apparatus set forth in claim 1 wherein said fastening member comprises a cover screw adapted to serve as a healing cap for said fixture following first stage surgery in the procedure of installing said dental implant in the patient's mouth.

7. The apparatus set forth in claim 6 wherein said first end of said passageway opens in an exposed upper surface of said screw, and wherein said seal means is disposed in said first end of said retrieval passageway adjacent said upper surface of said screw.

8. The apparatus set forth in claim 1 wherein said fastening member comprises an abutment screw and wherein said head means thereof is adapted to clamp an abutment onto the distal end of said fixture.

9. The apparatus set forth in claim 1 wherein said fastening member comprises a coping retaining screw and wherein said head means thereof is adapted to clamp a coping onto the gingival end of an abutment mounted on said implant fixture.

10. The apparatus set forth in claim 1 wherein said fastening member comprises an abutment screw and wherein said head means thereof is adapted to clamp an abutment onto the gingival end of said fixture, said second end of said passageway opens in an exposed surface of said screw, and wherein said seal means is disposed in said first end of said retrieval passageway.

11. The apparatus set forth in claim 1 wherein said fastening member comprises a coping retaining screw and wherein said head means thereof is adapted to clamp a coping onto the gingival end of said abutment, said first end of said passageway opens in an exposed upper surface of said screw head means, and wherein said seal means is disposed in said first end of said retrieval passageway adjacent said upper surface of said screws head means.

12. The apparatus set forth in claim 1 wherein said fastening member comprises an abutment screw and said apparatus further includes an abutment clamped by said head means of said abutment screw onto the gingival end of said fixture.

13. In dental implant apparatus of the type comprising:
(a) an implant fixture configured at least at a distal end thereof for implanted anchoring in a jawbone of a patient and having all internally threaded bore axially disposed therein and opening centrally through a gingival end of said fixture, and
(b) a threaded fastening member comprising an abutment screw having a distal end portion, an axially opposite gingival end portion and an externally threaded shank portion located axially between said ends and removably threadably engaged in the internal threads of said fixture bore, said gingival end portion normally protruding out of the bore opening and including head means thereon configured for rotating said abutment screw relative to said fixture by engagement with a fastener rotating tool, and
(c) an abutment clamped by said head means of said abutment screw onto the gingival end of said fixture; the improvement in combination therewith of:
(d) a retrieval passageway extendible axially through said abutment screw, said passageway opening at first and second axially opposite ends respectively in the gingival and distal end portions of said abutment screw, said passageway having a cross sectional configuration whereby an in situ fractured distal end portion segment of said abutment screw, remaining in said fixture bore after removal of the associated gingival end portion fractured abutment screw segment from said fixture bore, can be retrieved by inserting a cooperatively shaped working end of a retrieval tool into the access opening formed by said retrieval passageway intersecting the fracture surface of the distal end portion segment to thereby unscrew and thus retrieve the distal end portion segment from said fixture bore.

14. The apparatus set forth in claim 13 wherein said abutment screw has a threaded bore in said head means forming a continuation of said retrieval passageway, and further includes a prosthetic retaining screw having a threaded shank portion received in said head bore of said abutment screw and clamping a prosthetic coping onto the gingival end of said abutment.

15. The apparatus set forth in claim 14 wherein said prosthetic retaining screw also has a retrieval passageway extending axially therethrough and opening at first and second axially opposite ends respectively in the distal and gingival ends of said retaining screw.

16. The apparatus set forth in claim 15 wherein first seal means are disposed in said first end of said retaining screw retrieval passageway.

17. The apparatus set forth in claim 16 wherein second seal means are disposed in said second end of said retaining screw retrieval passageway.

18. The apparatus set forth in claim 13 further including in combination therewith a retrieval tool comprising a handle, a shank protruding axially from one end of said handle and having a termination at its free end formed by a tip portion, one of said shank and shank tip portions being constructed and arranged for entry axially into the access opening for engagement with the portion of the retrieval passageway remaining in the fractured segment for torque-transmittal engagement therewith for rotating such segment in unscrewing direction upon like rotation applied to the handle of said tool.

19. The apparatus set forth in claim 18 wherein said tool shank is cylindrical and has an outside dimension adapted for a close clearance fit within the internal threads of said implant fixture, and wherein said tip portion is sized in cross section for entry into the access hole.

20. The apparatus set forth in claim 18 wherein said retrieval passageway has a non-circular cross section and said shank of said tool has a cross sectional configuration complemental to that of said retrieval passageway and is dimensioned for a close clearance sliding fit thereinto.

21. In dental implant apparatus of the type comprising:
(a) an implant configured at least at a distal end thereof for implanted anchoring in a jawbone of a patient and having an internally threaded bore axially disposed therein and opening centrally through a gingival end of said fixture, and
(b) a threaded fastening member having a distal end portion, an axially opposite gingival end portion and an externally threaded shank portion located axially between said ends and removably threadably engaged in the internal threads of said fixture bore, said gingival end portion normally protruding out of the bore opening and including head means thereon configured for rotating said fastening member relative to said fixture by engagement with a fastener rotating tool; the improvement in combination therewith of:
(c) a retrieval passageway extending axially through said fastening member, said passageway opening at first and second axially opposite ends respectively in the distal and gingival end portions of said fastening member, said passageway having a cross sectional configuration whereby an in situ fractured distal end portion segment of said fastening member remaining in said fixture bore after removal of the associated gingival end portion fractured fastener segment from said fixture bore, can be retrieved by inserting a cooperatively shaped working end of a retrieval tool into the access opening formed by said retrieval passageway intersecting the fracture surface of the distal end portion segment to thereby unscrew and thus retrieve the distal end portion segment from said fixture bore, said apparatus further including in combination therewith a retrieval tool comprising a handle, a shank protruding axially from one end of said handle and having a termination at its free end formed by a tip portion, one of said shank and shank tip portions being constructed and arranged for entry axially into the access opening for engagement with the portion of the retrieval passageway remaining in the fractured segment for torque-transmittal engagement therewith for rotating such segment in unscrewing direction upon like rotation applied to the handle of said tool, wherein said tool shank is cylindrical and has an outside dimension adapted for a close clearance fit within the internal threads of said implant fixture, and wherein said tip portion is sized in cross section for entry into the access hole.

22. The apparatus set forth in claim 21 wherein said tool tip portion has a cross sectional configuration complemental to that of said retrieval passageway and is sized for a close sliding fit thereinto via the access opening.

23. The apparatus set forth in claim 21 wherein said tip portion is formed with easy-out auger teeth threaded in the opposite hand from that of the external threads of the shank portion of the fastening member.

24. In dental implant apparatus of the type comprising:
(a) an implant fixture configured at least at a distal end thereof for implanted anchoring in a jawbone of a patient and having an internally threaded bore axially disposed therein and opening centrally through a gingival end of said fixture, and
(b) a threaded fastening member having a distal end portion, an axially opposite gingival end portion and an externally threaded shank portion located axially between said ends and removably threadably engaged in the internal threads of said fixture bore, said gingival end portion normally protruding out of the bore opening and including head means thereon configured for rotating said fastening member relative to said fixture by engagement with a fastener rotating tool; the improvement in combination therewith of;
(c) a blind end retrieval passageway extending axially in said fastening member, said passageway being closed at a blind end thereof disposed axially distant from said distal end and opening at an axially opposite end in the gingival end portion of said fastening member, said passageway having a cross sectional configuration whereby an in situ fractured distal end portion segment of said fastening member, remaining in said fixture bore after removal of the associated gingival end portion fractured fastener segment from said fixture bore, can be retrieved by inserting the working end of a retrieval tool into the access opening formed by said retrieval passageway intersecting the fracture surface of the distal end portion segment to thereby unscrew and thus retrieve the distal end portion segment from said fixture bore, and
(d) further including seal means disposed in said retrieval passageway adjacent said gingival end portion and being constructed and arranged to block flow of liquid or debris past said seal means in said retrieval passageway.

25. A method of retrieving an in situ fractured segment of a fastening member in a dental implant assembly having an implant fixture configured at least at a distal end thereof for implanted anchoring in a jawbone of a patient and having an internally threaded bore axially disposed therein and opening centrally through a gingival end of such fixture, and further having a threaded fastening member with an externally threaded shank portion removably threadably engaged in the internal threads of the fixture bore and with a gingival end portion protruding out of the bore opening including head means thereon configured for rotating the fastener member relative to the fixture by engagement with a fastener rotating tool, said method comprising the steps of:

(a) providing a retrieval passageway in the fastener member extending axially therein and opening at least one end of one of the end portions of the fastening member and extending axially of said member at least for an axial length generally coextensive with the externally threaded shank portion of said member, (b) providing a retrieval tool having a handle for manually rotating the same about its axis and a shank coaxial with the handle and protruding therefrom adapted for insertion into the internally threaded bore of the fixture with clearance relative to the internal threads in the fixture bore, (c) forming the retrieval passageway and the shank portion of said retrieval tool each with a cross sectional configuration adapted to permit entry of the free working end of said shank portion into an access opening formed by the intersection of the retrieval passageway with the fracture surface of the fastener member and accessible subsequent to removal of the associated fractured segment of the fastener member originally disposed between the fracture and the gingival end portion of the fastener member, and (d) producing torque transmitting engagement of the working end of the tool and the portion of the retrieval passage remaining between the access opening and the distal end portion of the fastener member and rotating the in situ fragment segment in unscrewing direction toward the gingival end of the fixture until the segment has been cleared from the internal threads of said fixture.

26. A retrieval tool for use with dental implant apparatus of the type comprising:

(a) an implant fixture configured at least at a distal end thereof for implanted anchoring in a jawbone of a patient and having an internally threaded bore of a given constant diameter and being axially disposed therein and opening centrally through a gingival end of said fixture, and (b) a threaded fastening member having a distal end portion, an axially opposite gingival end portion and an externally threaded shank portion located axially between said ends and removably threadably engaged in the internal threads of said fixture bore, said gingival end portion normally protruding out of the bore opening and including heads means thereon configured for rotating said fastening member relative to said fixture by engagement with a fastener rotating tool, and (c) a retrieval passageway extending axially within through said fastening member, said passageway opening at least at a first axial end disposed in the gingival end portion of said fastening member, said passageway having a uniform cross sectional configuration throughout its axial extent in at least said distal end portion and being radially centered in said fastening member whereby an in situ fractured distal end portion segment of said fastening member, remaining in said fixture bore after removal of the associated gingival end portion fractured fastener segment from said fixture bore, can be retrieved by inserting the working end of a retrieval tool into the access opening formed by said retrieval passageway intersecting the fracture surface of the distal end portion segment to thereby unscrew and thus retrieve the distal end portion segment from said fixture bore (d) said retrieval tool comprising a handle, a shank protruding axially from one end of said handle and having an axial length dimension at least generally matching that of said externally threaded shank portion of said fastenin member and having a cross sectional dimension less than that of the fastening member bore, said shank having a termination at its free end much smaller in axial length dimension and cross sectional dimension than that of said shank and being constructed and arranged for entry axially into the access opening for engagement with the portion of the retrieval passageway remaining in the fractured segment for torque-transmittal engagement therewith for rotating such segment in unscrewing direction upon like rotation applied to the handle of said tool and wherein said tool shank is cylindrical and has an outside diametrical dimension sized slightly less than said threaded bore constant diameter for a close clearance fit within the internal threads of said bore of said implant fixture and wherein said shank termination comprises a tip portion centered radially of said tool shank and sized in cross section for entry into the access holes whereby insertion of said shank in said threaded bore automatically aligns said tip portion with said access hole and prevents said tip portion from striking and possibly damaging said internal threads of said bore of said implant fixture.

27. The tool set forth in claim 26 wherein said tool tip portion has a cross sectional configuration complemental to that of said retrieval passageway and is sized for a close sliding fit thereinto via the access opening.

28. The tool set forth in claim 26 wherein said tip portion is formed with easy-out auger teeth threaded in the opposite hand from that of the external threads of the shank portion of the fastening member.

29. The tool set forth in claim 26 for use with a retrieval passageway having a non-circular cross section and wherein said retrieval passageway has a non-circular cross section and said shank of said tool has a cross sectional configuration complemental to that of said retrieval passageway and is dimensioned for a close clearance sliding fit thereinto.

30. The tool of clam 26 wherein said shank has tooth means on the distal end of said shank arrayed radially outwardly of said tip portion and offset axially from the free end of said tip portion a given distance toward said shank.

31. An abutment screw for dental implant apparatus of the type comprising:

an implant fixture configured at least at a distal end thereof for implanted anchoring in an jawbone of a patient and having an internally threaded bore axially disposed therein and opening centrally through a gingival end of said fixture, and an abutment clamped by aid abutment screw into the gingival end of the fixture, said abutment screw having a distal end portion, an axially opposite gingival end portion and an externally threaded shank portion located axially between said ends and adapted to be removably threadably engaged in the internal threads of said fixture bore with said gingival end portion normally protruding out of the bore opening and including head means thereon configured for rotating said abutment screw relative to the fixture by engagement with an abutment screw rotating tool, a retrieval passageway extending axially within said abutment screw, said passageway opening to the exterior of said abutment screw at first least at a axial end generally disposed in the gingival end portion of said abutment screw, said passageway having a cross sectional configuration whereby an in situ fractured distal end portion segment of said abutment screw, when remaining in the fixture bore after removal of the associated gingival end portion fractured abutment screw segment from the fixture bore, can be retrieved by inserting the working end of a retrieval tool into the access opening formed by said retrieval passageway intersecting the fracture surface of the distal end portion segment to thereby unscrew and thus retrieve the distal end portion segment from the fixture bore, said abutment screw further including seal means disposed in said retrieval passageway and being constructed and arranged to block flow of liquid or debris past said seal means in said retrieval passageway.

* * * * *

UNITED STATES PATENT AND TRADEMARK OFFICE
CERTIFICATE OF CORRECTION

PATENT NO. : 5,951,287
DATED : September 14, 1999
INVENTOR(S) : Roy T. Hawkinson It is certified that error appears in the above-identified patent and that said Letters Patent is hereby corrected as shown below:

Column 5, line 33, after "through" delete "(i) and insert therefore --(f)--.

IN THE CLAIMS:

Column 14, line 35, delete "fastenin" and insert therein --fastening--.

Column 14, line 44, delete "mears" and insert therein --means--.

Column 14, line 48, delete "sectionial" and insert therein --sectional--.

Column 15, line 27, delete "screws" and insert therein --screw--.

Column 15, line 36, after "having" delete "all" and insert therein --an--.

Column 15, line 53, after "passageway" delete "extendible" and insert therein --extending--.

Column 18, line 59, delete "through".

Column 19, line 12, after "said" delete "fastenin" and insert therein --fastening--.

Column 19, line 30, after "access" delete "holes" and insert therein --hole--.

Column 20, line 4, delete "clam" and insert therein --claim--.

Column 20, line 11, after "in" delete "an" and insert therein --a--.

Signed and Sealed this

Tenth Day of April, 2001

Attest:

NICHOLAS P. GODICI

Attesting Officer

Acting Director of the United States Patent and Trademark Office